United States Patent [19]

Andersson et al.

[11] Patent Number: 5,599,268
[45] Date of Patent: Feb. 4, 1997

[54] BELT DRIVEN LINEAR TRANSPORT APPARATUS FOR PACKAGING MACHINE

[75] Inventors: Roland J. E. Andersson, Arlington Heights; Shigehiro Kinoshita, Buffalo Grove, both of Ill.; David L. Persells, Twin Lakes, Wis.; Arde Kirka, Algonquin, Ill.

[73] Assignee: Tetra Laval Holdings & Finance S.A., Pully, Switzerland

[21] Appl. No.: 315,410

[22] Filed: Sep. 28, 1994

Related U.S. Application Data

[63] Continuation-in-part of Ser. No. 277,614, Jul. 20, 1994, Pat. No. 5,488,308.

[51] Int. Cl.⁶ .............................. B31B 1/52; B65B 43/28; B66B 11/06
[52] U.S. Cl. .......................... 493/184; 493/452; 493/162; 53/565; 414/627; 187/254; 187/261; 74/89.22
[58] Field of Search ...................................... 493/156, 157, 493/162, 183, 184, 465, 466, 452; 53/565, 371.7; 198/468 A, 468.8; 414/627; 187/251, 254, 261; 74/89.22, 89.2

[56] References Cited

U.S. PATENT DOCUMENTS

| | | | |
|---|---|---|---|
| 1,023,124 | 4/1912 | Clark | 187/251 |
| 1,422,816 | 7/1922 | Beers et al. | |
| 1,821,883 | 9/1931 | Enock | |
| 2,325,889 | 8/1943 | Thompson et al. | |
| 2,686,099 | 8/1954 | Bomberger et al. | |
| 3,003,357 | 10/1961 | Votta, Jr. | 74/95 |
| 3,488,098 | 1/1970 | Sobsczak | 74/89.2 |
| 3,500,692 | 3/1970 | Sangster et al. | 74/89.22 |
| 3,614,898 | 10/1971 | Paine | 74/89.2 |
| 3,698,542 | 10/1972 | Reger et al. | |
| 4,042,124 | 8/1977 | Bowdry, III et al. | |
| 4,161,004 | 7/1979 | Dailziel | 360/106 |
| 4,219,301 | 8/1980 | Freeman | |
| 4,404,863 | 9/1983 | James | 74/89.22 |
| 4,534,706 | 8/1985 | Palm et al. | 74/89.22 |
| 4,537,084 | 8/1985 | Passemard | 74/89.22 |
| 4,603,772 | 8/1986 | Tomosue | |
| 4,712,665 | 12/1987 | McDonald et al. | |
| 4,765,452 | 8/1988 | Johansson | |
| 4,837,650 | 6/1989 | Kawada | 79/89.2 |
| 4,991,116 | 2/1991 | Hohner | |
| 5,020,169 | 6/1991 | Hamada et al. | 5/10.2 |
| 5,072,410 | 12/1991 | Vachris et al. | |
| 5,163,121 | 11/1992 | Hosler | |
| 5,215,181 | 6/1993 | Blatt | |
| 5,336,029 | 8/1994 | Kato et al. | 414/627 |
| 5,371,452 | 12/1994 | Kato | 318/610 |

*Primary Examiner*—Jack W. Lavinder
*Assistant Examiner*—Christopher W. Day
*Attorney, Agent, or Firm*—McAndrews, Held & Malloy, Ltd.; Patrick N. Burkhart

[57] ABSTRACT

A linear drive apparatus for moving a canon in a packaging machine from a first position to a second position is set forth. The apparatus includes first and second spaced apart guide rods and an engagement assembly that is disposed between and slidably engages the first and second guide rods. The engagement assembly is adapted to engage one or more cartons for movement between the first and second positions. The apparatus further includes a drive shall onto which a drive roller is disposed for co-rotation. A first drive belt is connected to the drive roller and disposed about the drive roller in a clockwise direction at a first end thereof while a second end of the first drive belt is connected to a first portion of the engagement assembly. A second drive belt is connected to the drive roller and disposed about the drive roller in a counter-clockwise direction at a first end thereof while a second end of the second drive belt is connected to a second portion of the engagement assembly opposite the first portion of the engagement assembly. The rotation of the drive shaft in a clockwise direction causes linear movement of the engagement assembly in a first direction along the guide rods and the rotation of the drive shaft in a counter-clockwise direction causes linear movement of the engagement assembly in a second direction opposite the first direction.

55 Claims, 18 Drawing Sheets

FILL LIFT POSITION PROFILE

FILL LIFT ACCELERATION PROFILE

BOTTOM LIFT POSITION PROFILE

BOTTOM LIFT VELOCITY PROFILE

BOTTOM LIFT ACCELERATION PROFILE

TOP PREFOLDER POSITION PROFILE

TOP PREFOLDER VELOCITY PROFILE

TOP PREFOLDER ACCELERATION PROFILE

BELT DRIVEN LINEAR TRANSPORT APPARATUS FOR PACKAGING MACHINE

CROSS-REFERENCE TO RELATED APPLICATIONS

This application is a continuation-in-part of U.S. Ser. No. 08/277,614, filed Jul. 20, 1994 (Attorney Docket No. 10319US01—Corporate Docket No. TRX-0040). Now U.S. Pat. No. 5,488,308.

TECHNICAL FIELD

The present invention relates to a belt driven linear transport apparatus. More specifically, the present invention relates to an apparatus for linearly driving a carton engagement mechanism in a packaging machine.

BACKGROUND

Packaging machines are known that integrate the various components necessary to fill and seal a container into a single machine unit. This packaging process, generally stated, includes feeding carton blanks into the machine, sealing the bottom of the cartons, filling the cartons with the desired contents, sealing the tops of the cartons, and then off loading the filled cartons for shipping.

Many packaging machines require one or more linearly driven mechanisms that assist in the various packaging processes. One such mechanism is set forth in U.S. Pat. No. 4,712,665 to McDonald et al. The '665 patent illustrates a container lifting mechanism that includes a vertical tube actuator that is slidably mounted in bearings within a fixed sleeve. A second vertical tube actuator is slidably mounted in bearings within the first vertical tube to have independent vertical movement relative thereto. Vertical linear movement of the carton is accomplished by hydraulic activation of the first and second vertical tube actuators.

Another linearly driven mechanism for use in a packaging machine is set forth in U.S. Pat. No. 4,738,077 to Wakbayashi et al. The '077 patent illustrates an apparatus for forming containers, particularly gable top containers. The apparatus uses a linearly driven fork that pre-folds opposed side panels of the gabled portion of the container. The linear movement mechanism that is used to linearly drive the fork is hydraulically actuated.

In addition to the foregoing hydraulically operated linear actuators, other linear drive mechanisms may be utilized in packaging machines. Such mechanisms include ball screws and linear motors.

Trends within the field of packaging machines point toward increasingly high capacity machines intended for rapid, continuous filling and sealing of a very large number of identical or similar packaging containers, e.g., containers of the type intended for liquid contents such as milk, juice, and the like. The increased throughput and decreased size requirements have increased the demands that are placed on the linear drive mechanisms that are employed. For example, high precision linear movement with little allowable backlash is often desirable and/or required. Likewise, low mass actuators are desirable to facilitate high speed movement of the driven components.

Additional limitations on the linear actuators are imposed by virtue of the hygienic nature of the packaging process. The linear actuators must be designed to limit their contamination of the interior of the packaging machine and, further, must be easily cleaned.

SUMMARY OF THE INVENTION

A linear drive apparatus for moving a carton in a packaging machine from a first position to a second position is set forth. The apparatus includes first and second spaced apart guide rods and an engagement assembly that is disposed between and slidably engages the guide rods. The engagement assembly is adapted to engage one or more cartons for movement between the first and second position. The apparatus further includes a drive shaft onto which a drive roller is disposed for co-rotation. A first drive belt is connected to the drive roller and disposed about the drive roller in a clockwise direction at a first end thereof while a second end of the first drive belt is connected to a first portion of the engagement assembly. A second drive belt is connected to the drive roller and disposed about the drive roller in a counter-clockwise direction at a first end thereof while a second end of the second drive belt is connected to a second portion of the engagement assembly opposite the first portion of the engagement assembly. The rotation of the drive shaft in a clockwise direction causes linear movement of the engagement assembly in a first direction along the guide rods and the rotation of the drive shaft in a counter-clockwise direction causes linear movement of the engagement assembly along the guide rods in a second direction opposite the first direction.

In accordance with one embodiment of the apparatus, the engagement assembly includes first and second legs slidably engaging the first and second guide rods. A bar extends between the first and second legs and, for example, may include one or more forked folder arms that respectively engage and pre-fold a carton. One or more carton grippers that grip the fin of a gabled section of the carton may also, or in the alternative, extend from the engagement bar. Other carton engagement adaptations are also suitable for use in the disclosed apparatus.

In a still further embodiment of the apparatus, a further drive roller is disposed for co-rotation with the drive shaft. A further pair of drive belts extend from the further drive roller, one belt extending from and about the further drive roller in a clockwise direction and the other belt extending from and about the further drive roller in a counter-clockwise direction. Both belts extend from the further drive roller to engage respective portions of the engagement assembly. The points of engagement between all of the drive belts and the engagement assembly form the corners of a parallelogram, such as a rectangle.

The apparatus may be subject to control by a control system that controls the rotation of the drive shaft. The control system may include a servomotor connected to rotationally drive the drive shaft and a servo amplifier connected to control the operation of the servomotor. A programmable axis manager ("PAM") may be connected to control the operation of the servo amplifier to cause the servomotor to execute user programmed motion profiles.

Other objects and advantages of the present invention will become apparent upon reference to the accompanying detailed description when taken in conjunction with the following drawings.

DETAILED DESCRIPTION OF THE PREFERRED EMBODIMENT

Figure 1:
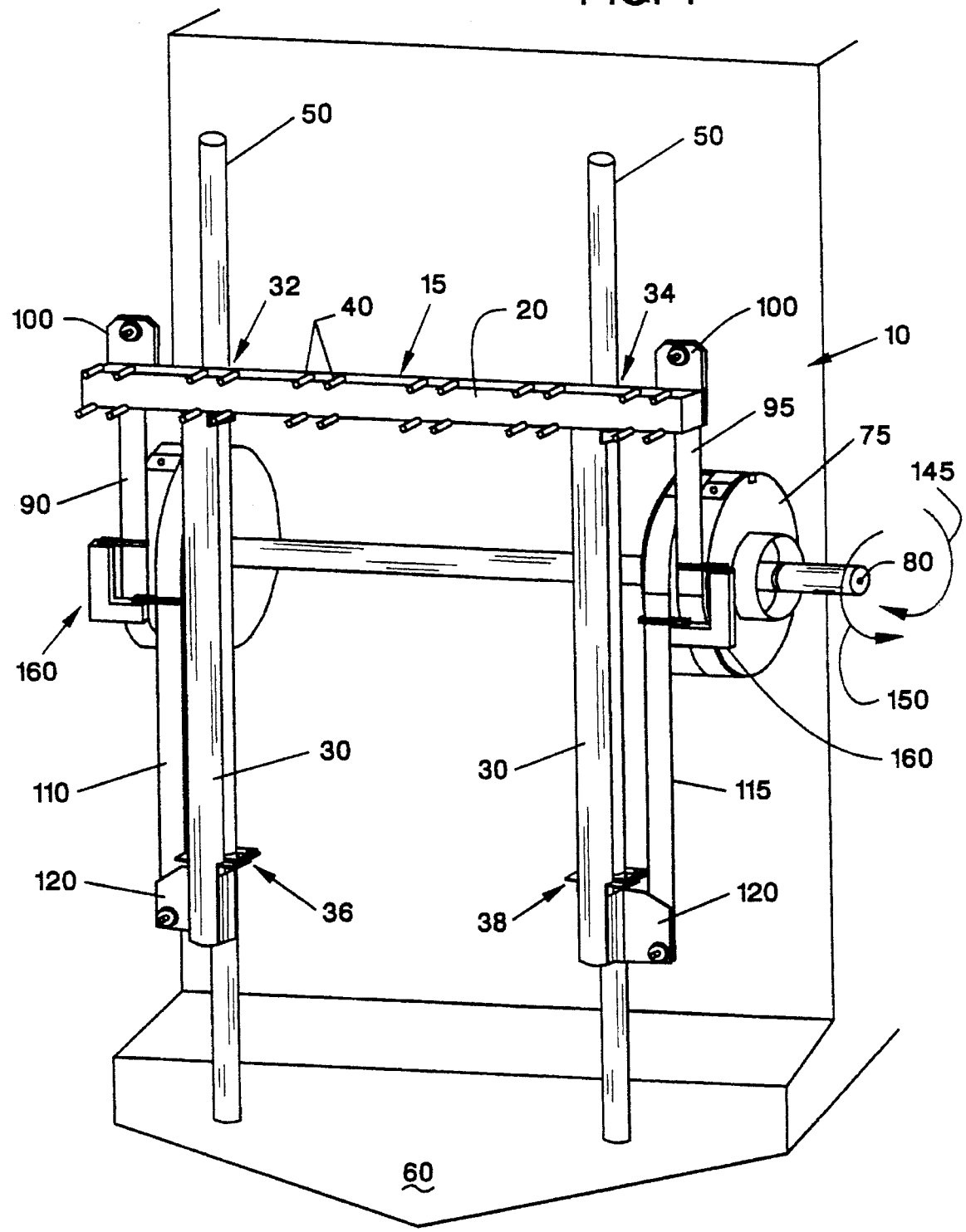
FIGS. 1 and 2 are perspective views of one embodiment of a belt drive linear transport mechanism.
Figure 2:
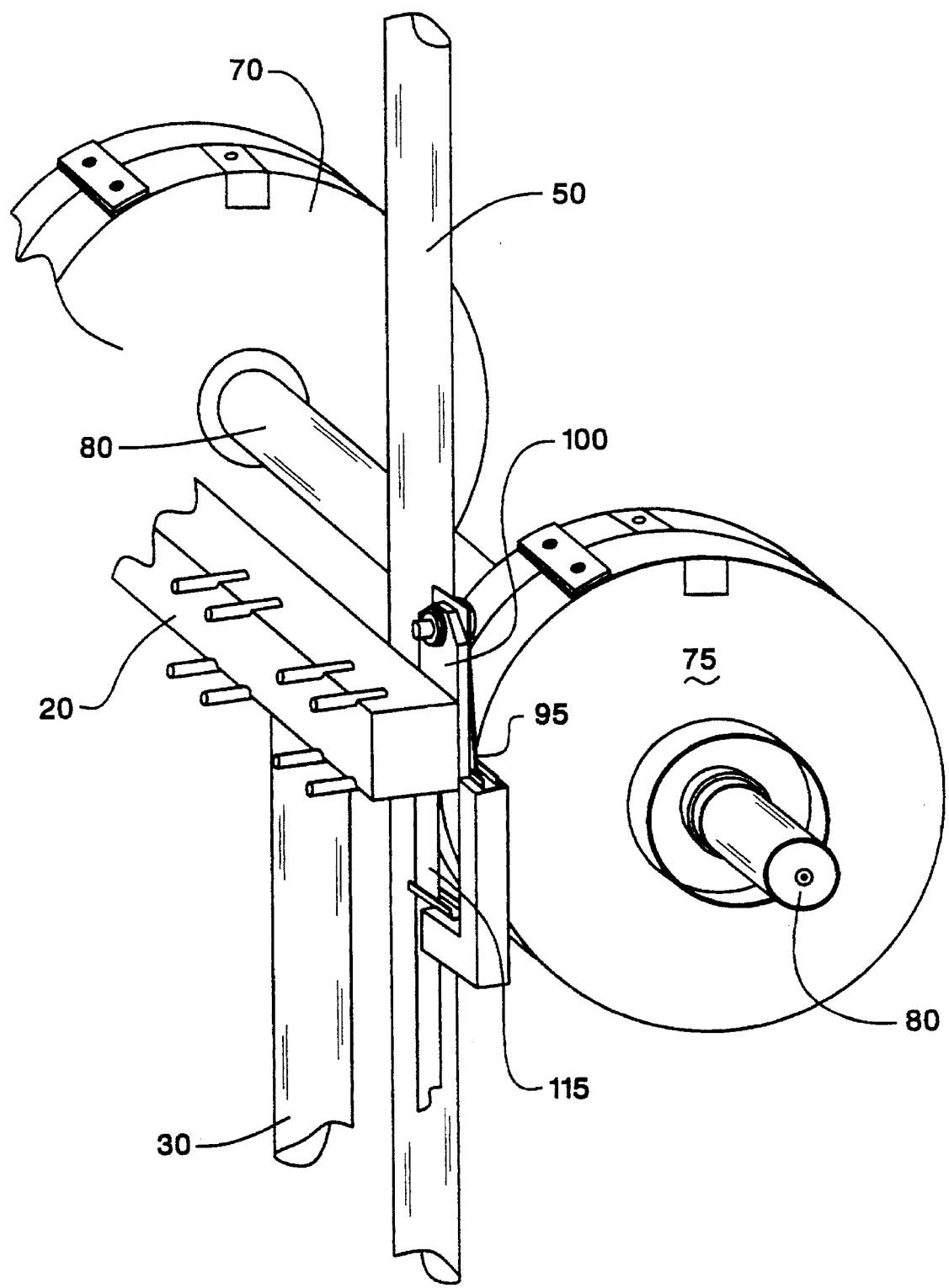

A linear drive mechanism, shown generally at 10, is illustrated in FIGS. 1 and 2. The drive mechanism 10 includes an engagement assembly 15. The engagement assembly 15, in turn, includes a horizontally disposed engagement bar 20 and a pair of spaced apart vertical legs 30 extending from the engagement bar 20. The bar 20 includes a plurality of pegs 40 that extend horizontally to engage, for example, various carton engagement attachments. A pair of vertically disposed guide rods 50 extend from a base 60 and engage the vertical legs 30 at portions 32, 34, 36, and 38 in a manner that allows the vertical legs 30 to slide along the guide rods 50.

A pair of drive rollers 70, 75 are disposed on opposite ends of a shaft 80 in a region exterior of the guide rods 50 for co-rotation with the shaft 80. Each of the drive rollers 70, 75 has a respective drive belt 90, 95 that extends about the respective drive roller 70, 75 in a clockwise direction to engage respective connecting tabs 100 on the bar 20. Each of the drive rollers 70, 75 also has a respective further drive belt 110, 115 that extends about the circumference of the respective drive roller 70, 75 in a counterclockwise direction to engage a respective connecting tab 120 on the vertical legs 30. The tabs 100 and 120 may lie in the same vertical plane and further may be disposed at the corners of a parallelogram, shown here as a rectangle.

Figure 3:
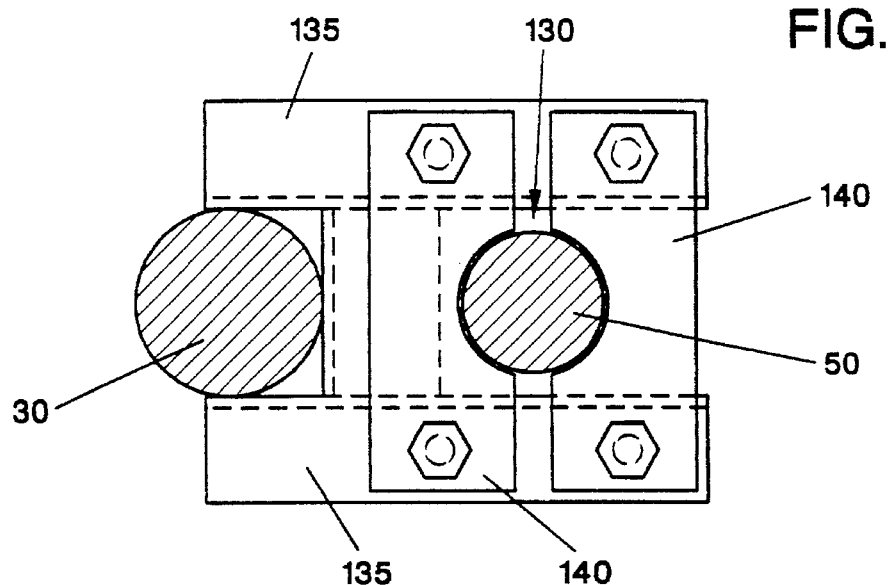
FIGS. 3 and 4 illustrate one type of connection that provides sliding engagement between the legs and guide rods.
Figure 4:
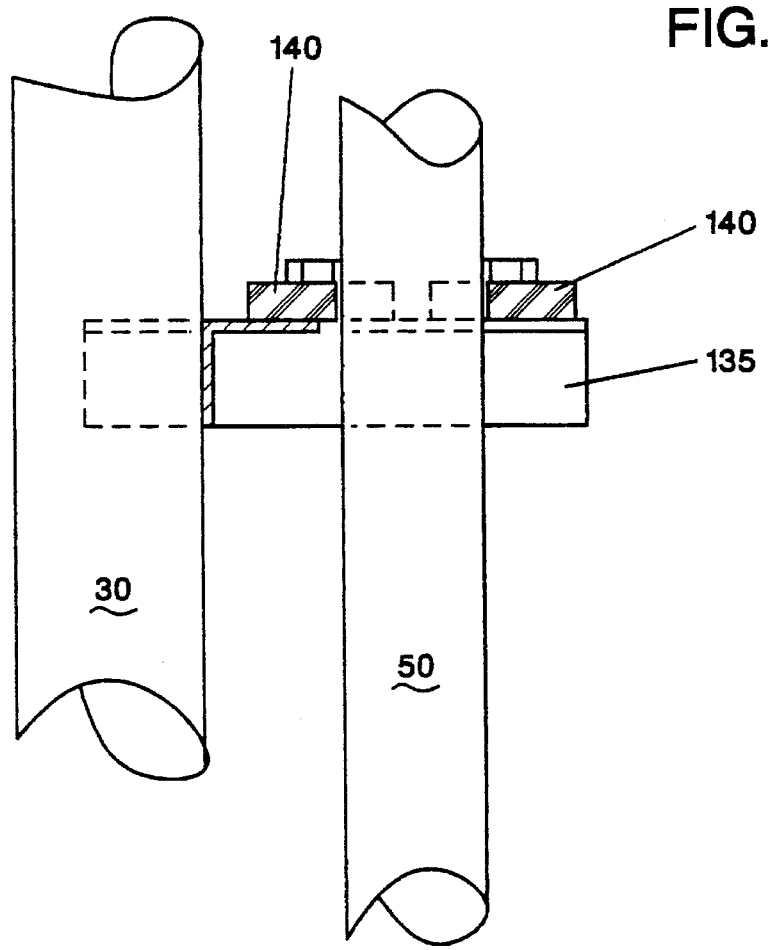

The slidable engagement between the vertical legs 30 and guide rods 50 is illustrated in FIGS. 3 and 4. Each of the legs 30 may include a forked protrusion 135 that, for example, is welded as part of the leg 30. The guide rod 50 sits in a channel 130 defined by forks 135. A pair of bushings 140 are disposed on opposite sides of the guide rod 50 in a direction transverse to the forks 135 and are secured, for example, by nuts and bolts, to the forks 135. The bushings 140 may be made from a material such as UHMW or nylon. Other materials are likewise suitable for such use.

Operation of the belt drive mechanism can be understood with reference again to FIG. 1. In operation, the shaft 80 is driven, for example, by a servomotor, in a cyclic fashion in both the clockwise and counterclockwise directions. When the shaft 80 is rotated in the clockwise direction, illustrated by arrow 145, the drive bands 110, 115 become shorter and exert an upward force on vertical legs 30 to cause the legs 30 and the bar 20 to proceed in an upward direction. At the same time, the drive bands 90, 95 are unrolled from the drive rollers 70, 75 and are effectively lengthened. When the shaft 80 is rotated in the counterclockwise direction, illustrated at arrow 150, the drive bands 110, 115 are unrolled from the respective drive rollers while the drive bands 90, 95 are rolled onto the respective drive rollers 70, 75. This effectively increases the length of drive bands 110, 115 and decreases the length of drive bands 90, 95 such that drive bands 90, 95 exert a downward force on the bar 20 and cause the bar 20 and the vertical legs 30 to slide in a downward direction along guide rods 50. The cyclic clockwise and counterclockwise rotation of the shaft 80 may occur at a high rate of speed with little, if any, backlash and with a high degree of precision of movement. The drive shaft 80, drive rollers 70 and 75, drive bands 90, 95, 110, and 115, and engagement assembly 15 may be made from stainless steel to facilitate easy cleaning of the apparatus.

Breakage of any of the bands 90, 95, 110, 115 may disrupt the operation of the linear drive mechanism 10 or may result in its complete failure. Such a failure may disrupt the operation of the entire packaging machine and/or may cause significant damage. As such, a plurality of band breakage detectors 160 are employed. The construction, operation, and relative position of the detectors 160 are more fully set forth in connection with U.S. Ser. No. 08/277,614, filed Jul. 20, 1994.

The linear drive mechanism 10 may be used in a variety of different types of packaging machines and for a variety of different purposes. One such machine is described in U.S. Pat. No. 5,488,812 which is hereby incorporated by reference. The machine described in the '546 application includes two endless belt conveyors that are vertically displaced from one another. The conveyors transport the cartons to a plurality of modular processing stations where the cartons are filled and sealed. A plurality of lifting mechanisms are employed to transfer cartons from a conveyor at one level to another conveyor at another level as well as for lifting the cartons during filling and top sealing. Additionally, a pre-folder is used to pre-fold the cartons as they are processed within the machine.

Figure 5:
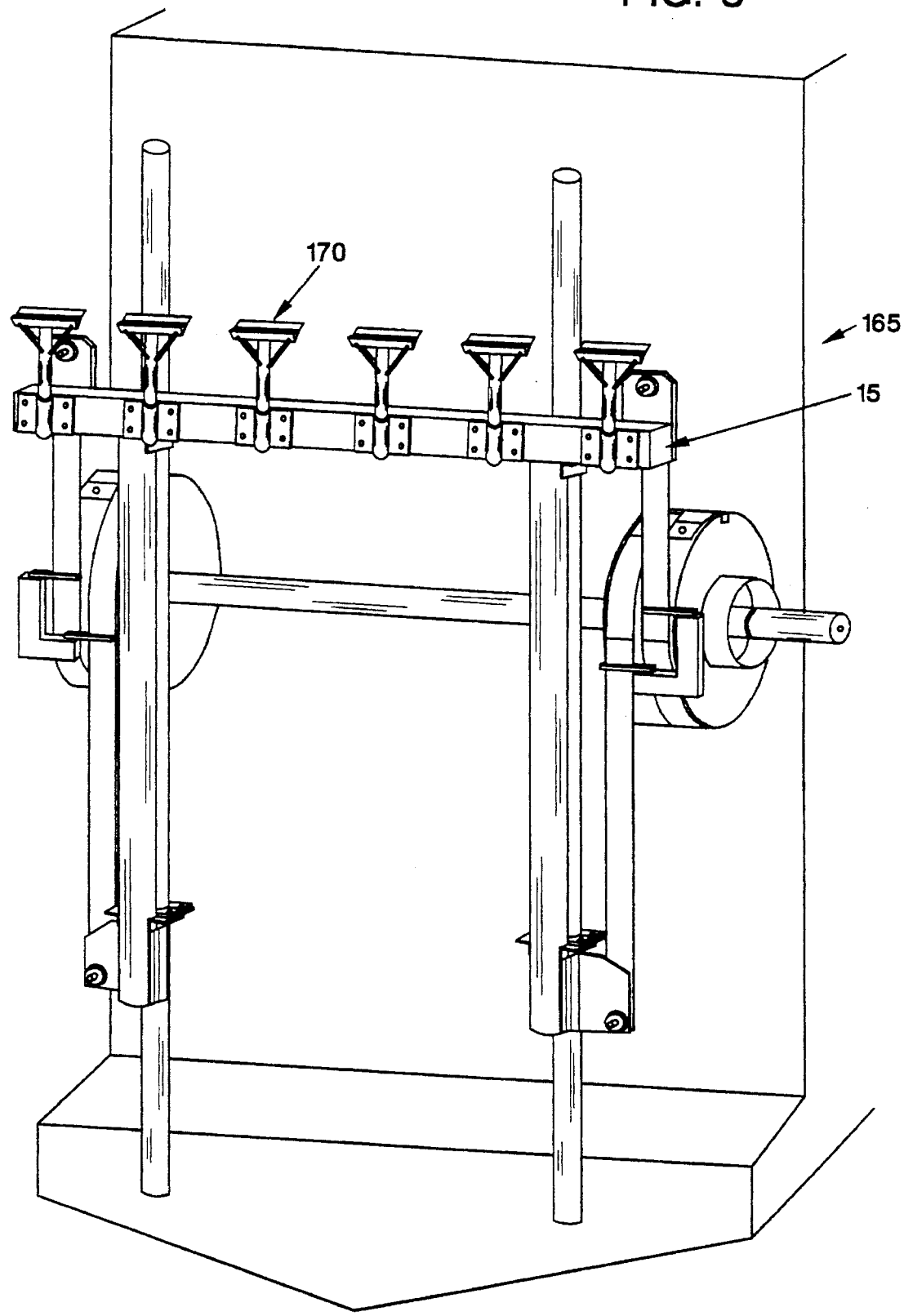
FIGS. 5 and 6 are perspective views of a canon lifter mechanism employing a belt driven linear transport mechanism.

A lifter mechanism that utilizes the presently described drive mechanism is illustrated in FIG. 5 at 165. The lifter mechanism 165 may be suitably substituted for one or more of the lifter mechanisms set forth in the '546 application.

Figure 6:
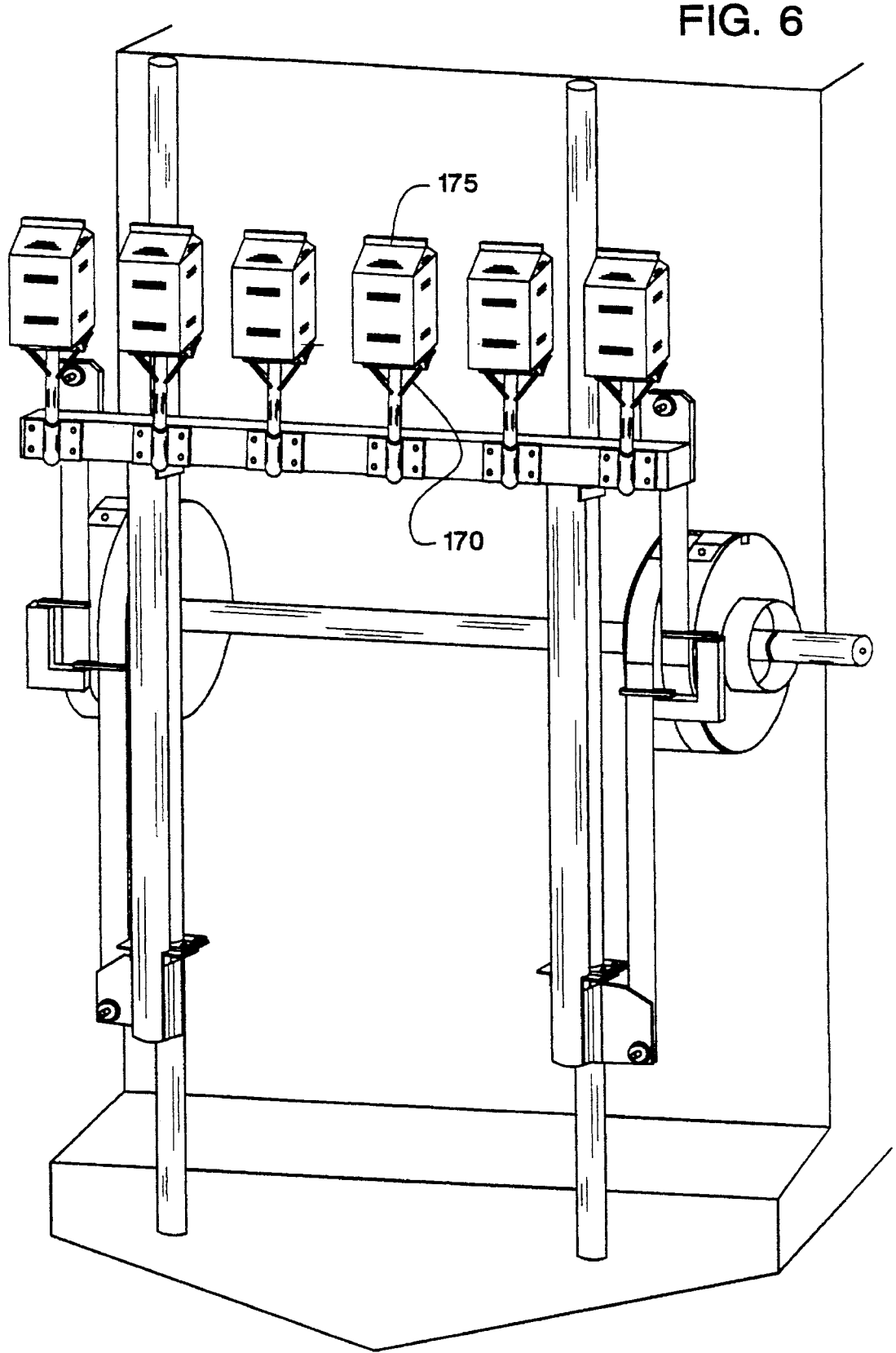

The lifter mechanism 165 is generally similar to the mechanism 10 of FIG. 1. The engagement assembly 15, however, includes a plurality of carton grippers 170 that are each shaped to grasp the bottom fin of a gabled container. FIG. 6 illustrates the lifter mechanism 165 engaging a plurality of gabled bottom cartons 175. The engagement between the carton grippers 170 and the bottom fin is more fully described in U.S. Pat. No. 5,517,801 entitled "Lifter Mechanism Employing a Carton Bottom Gripper and Canon Bottom Seal Configuration for Use Therewith", filed on even date herewith.

Figure 7:
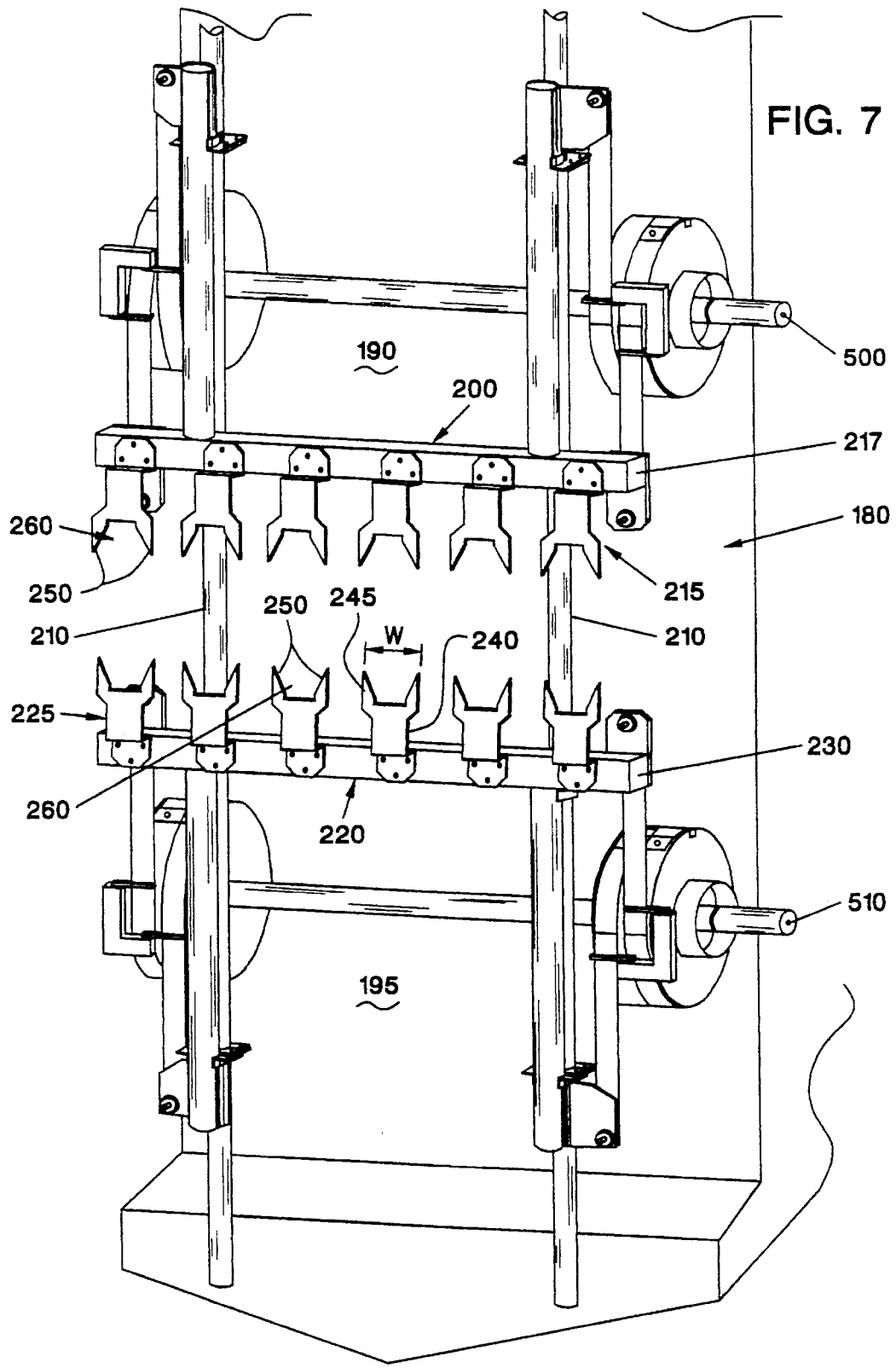
FIG. 7 is a perspective view of a canon lifter/pre-folder employing a belt driven linear transport mechanism.

FIG. 7 illustrates a pre-folder mechanism, shown generally at 180, that may be used in a packaging machine of the type disclosed in the aforementioned '546 application. The pre-folder mechanism utilizes both an upper and lower belt drive mechanism 190 and 195. The upper belt drive mechanism 190 includes an engagement assembly 200 that slidably engages a pair of spaced apart guide rods 210 in the aforesaid manner. The engagement assembly 200 includes a plurality of downwardly directed folder arms 215 secured to bar 217. Similarly, the lower belt drive mechanism 195 includes an engagement assembly 220 that slidably engages the guide rods 210. The engagement assembly 220 includes a plurality of upwardly directed folder arms 225 secured to bar 230. Each of the engagement assemblies 200 and 220 are movable toward and away from one another through operation of the respective belt drive mechanism 190 and 195.

Each of the upwardly directed and downwardly directed folder arms 215 and 225 includes a body portion 240 connected to the respective bar 217 and 230 and a head portion 245 extending from the body portion 240. The head portion 245 has a width W that, for example, corresponds to the width of a carton carrier such as is shown in the previously described '546 application. A pair of forks 250 define a generally V-shaped recess 260 in the head portion 245 of each of the folder arms 215 and 225. The interior sidewalls of the forks 250 that define the V-shaped recess 260 of each folder arm 215 engage opposed side panels at the top of the respective carton to pre-fold the carton top toward its characteristic gabled shape. Likewise, the interior sidewalls of the forks 250 that define the V-shaped recess 260 of each folder arm 225 engage opposed side panels at the bottom of the respective carton to pre-fold the carton bottom toward its characteristic gabled shape.

Figure 8:
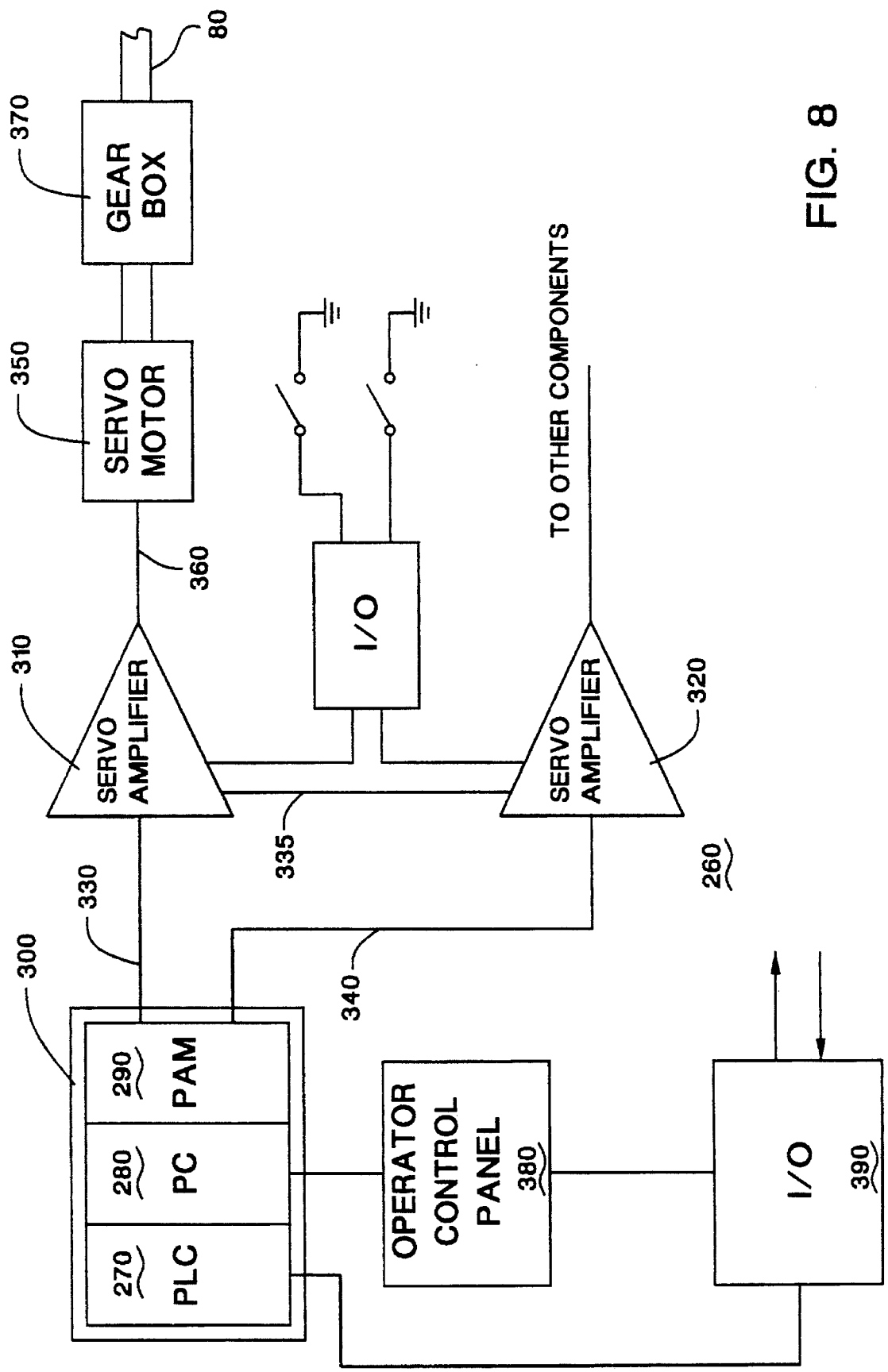
FIG. 8 is a schematic block diagram of one type of control system for driving the lifter mechanism of FIGS. 5 and 6.

FIG. 8 is a schematic block diagram illustrating one embodiment of a control system suitable for operation and control of the lifter mechanism 165 illustrated in FIG. 5. The control system, shown generally at 260, may include a PLC 270, an industrial PC 280, and a programmable axis controller ("PAM") 290, all of which are connected for communication with one another in a VME bus rack 300. The PAM 290 is further connected for communication with and for control of one or more servo amplifiers 310 and 320, the PAM 290 being connected respectively to each servo amplifier along one or more lines 330, 335, and 340 that, for example, may be an optical ring network. Servo amplifier 310 is connected to control the operation of a servomotor 350 along one or more lines 360. The servomotor 350, in turn, may directly rotate the drive shaft 80 or rotate the drive shaft 80 through an intermediate gear box 370. The control system may be constructed and operated pursuant to the teachings of U.S. Ser. No. 08/315,414 entitled "Control System for a Packaging Machine", filed on even date herewith and incorporated by reference.

In the illustrated embodiment, the PAM 290, servo amplifier 310, and servomotor 350 may be selected from any number of commercially available products, the specific interconnection being dependent on the products selected and, further being within the skill of those familiar with such servocontrol systems. The PAM 290, for example, may be a PAM available from Socapel. Similarly, the servo amplifier 310 may be, for example, a Model ST-1 amplifier available from Socapel. The lifter mechanism 165 connected to servomotor 350 moves in accordance with a desired motion profile that is stored in the PAM 290. The PAM software executes this motion profile through its control of the servo amplifier 310.

Other ancillary components are also associated with the control system 260. These ancillary components include the PLC 270 and industrial PC 280. The industrial PC 280 may be used in the control system 260 to control the operation of a video monitor on an operator control panel 380 that communicates machine status information to the user. The PLC 270 may be connected through an I/O control board 390 to monitor various sensors distributed throughout, for example, the packaging machine described in the previously mentioned '546 application and, further, to send various control signals to the various packaging machine components. The PLC 270 may also function to monitor keypresses of keyswitches on the operator control panel 380, as well as other system input. One type of PLC suitable for such control and operation is a Model 9070 manufactured by GE Fanuc.

Figure 9:
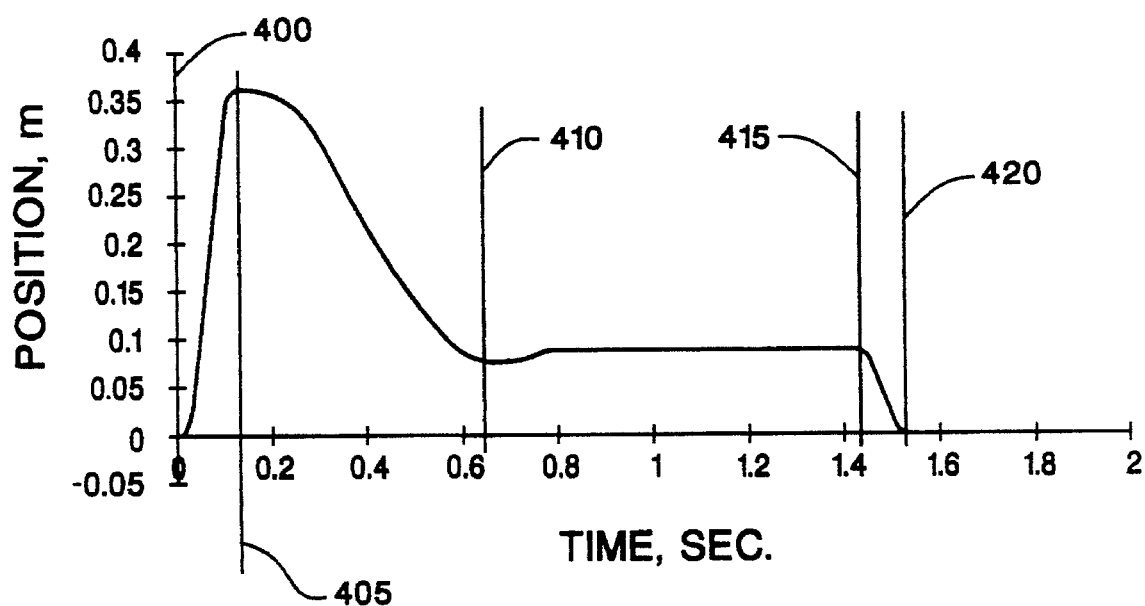
FIGS. 9–11 are graphs illustrating motion profiles that can be used in the control system of FIG. 8 to drive the lifter mechanism of FIGS. 5 and 6.
Figure 10:
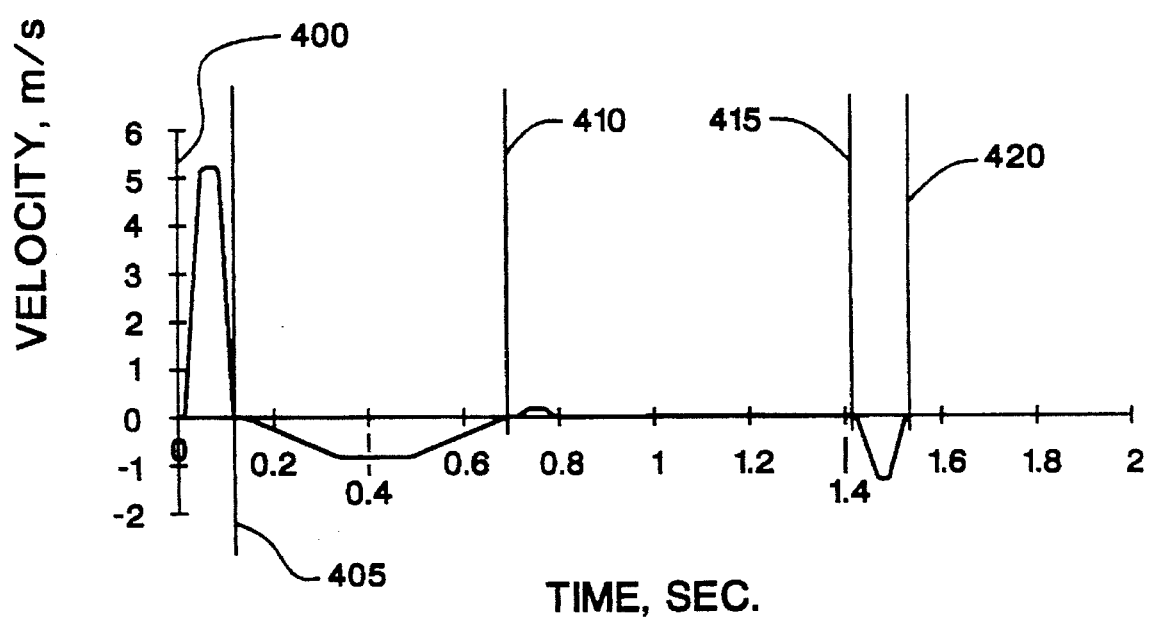
Figure 11:
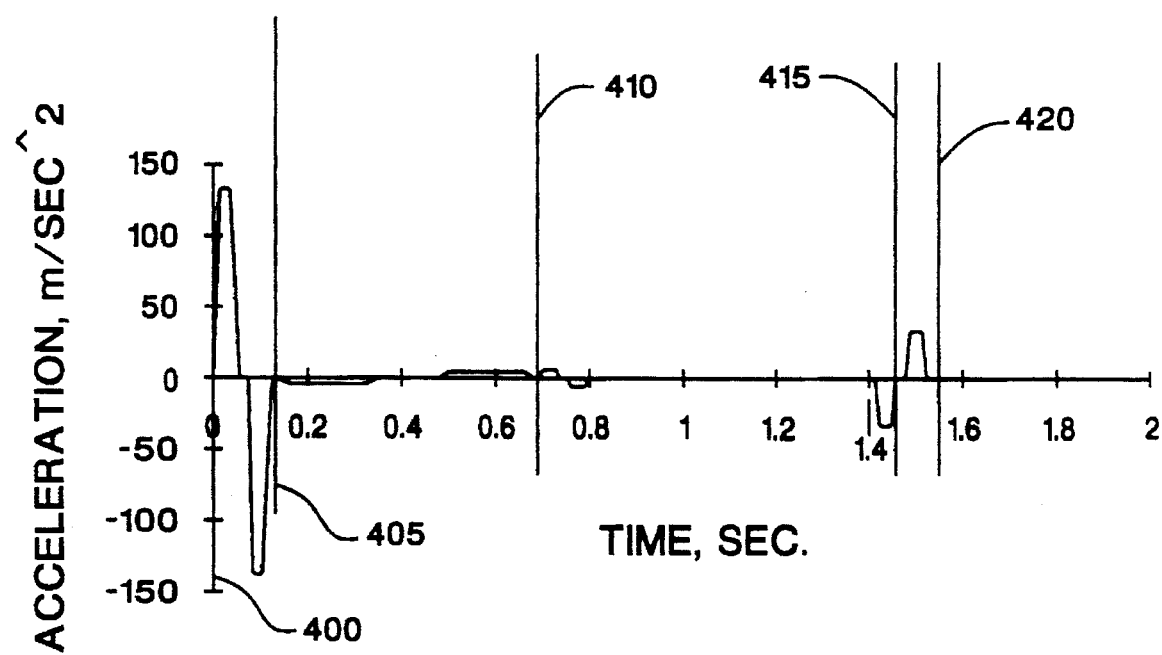

When the lifter mechanism 165 is used to lift a carton for filling and sealing, for example, in the packaging machine set forth in the previously mentioned '546 application, the motion profile may include four moves. The acceleration, velocity, and position profiles are set forth in FIGS. 9 and 11. The first motor move, shown between lines 400 and 405 of each of FIGS. 9 and 11, drives the carton grippers 170 and cartons 175 up through the upper band and into fill chambers for filling of the cartons through a plurality of fill nozzles. The distance moved is sufficient to bring the carton bottoms within a few mm of the bottom of the fill nozzle.

This first move drives carton grippers 170 up as quickly as possible. The accelerations have been ramped and made as small as possible to both minimize stress on the bands and couplings and to minimize demands on amplifier current. The accelerations cannot be made smaller without increasing the maximum velocity to levels that could require more voltage than the amplifier 310 can provide.

The second move, illustrated between lines 405 and 410, draws the canon grippers 170 down from the fill nozzle. It begins slightly after filling begins. The second move draws the carton grippers 170 down from the fill nozzle at velocities sufficient to keep the fill nozzle close to the liquid level. For hygiene reasons, the canon grippers 170 are prevented from rising to levels that immerse the outside of the nozzle in the liquid. To minimize splashing and foam, the canon grippers 170 move down slow enough to keep the liquid level close to the bottom of the nozzle. The second move ends when the top sealing areas of the canons are in the plane of the top sealer jaws of, for example, an ultrasonic top sealer.

The third move, shown between lines 410 and 415 drives the canon grippers 170 up a length sufficient to keep the top sealing surfaces of the canon in the same plane as the jaws of the top sealer during jaw closure. Without this upward move of the canon grippers 170, the top sealing surfaces of the carton may slide under the sealer jaws during their closure. The third move begins when the sealer jaws make contact with the top sealing surfaces of the canon.

The accelerations of the third move have been limited to 0.05 g since larger accelerations may cause the liquid to weigh more with respect to the canon. This may cause carton bulging that, in turn, may allow an excess amount of air to be trapped in the canon during sealing. Bulging cartons are undesirable because they are difficult to handle without damage and, further, because the bulging implies an internal pressure that can abet canon leaks, bulging also implies that there is extra oxygen in the canon that can oxidize the container contents. Further, food spray may result. Such food sprays are undesirable for hygiene reasons.

The fourth move, shown between lines 415 and 420, draws the carton grippers down to their home position sometime before the upper band moves. The retraction move begins after the sealing jaws have released the carton tops.

Each move of the lifter profile is principally a 40%, 20%, 40% trapezoidal velocity profile. However, during the time of any acceleration (or deceleration) 20% of the time is spent ramping up to constant acceleration. The ramping of accelerations was done to limit jerking of the mechanism and thereby prevent undue stress on its components.

Figure 12:
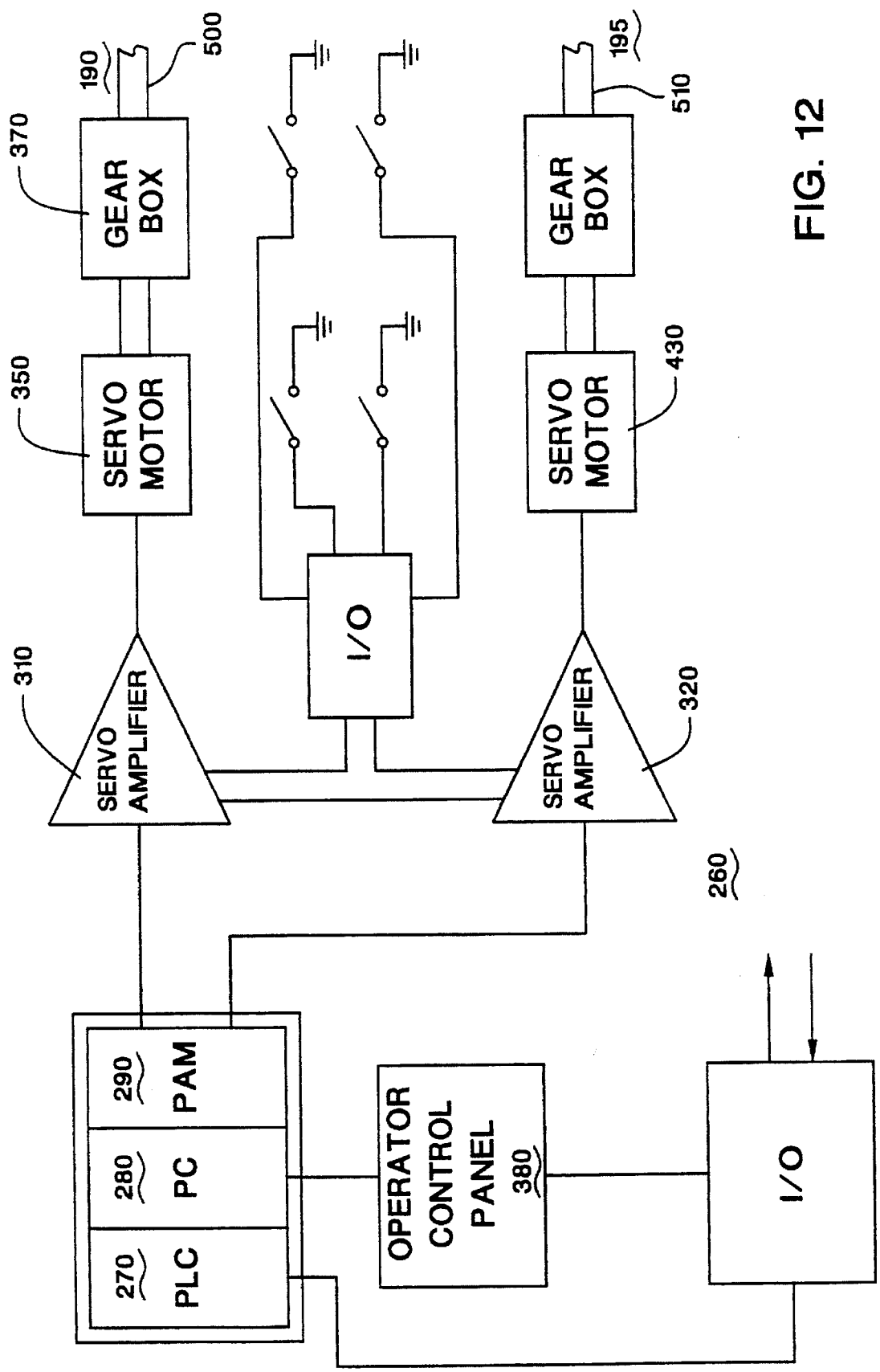
FIG. 12 is a schematic block diagram of one type of control system for driving the lifter/pre-folder illustrated in FIG. 7.

FIG. 12 illustrates a block diagram of a control system for use with the pre-folder mechanism 180 shown in FIG. 7. In this embodiment, servomotor 350 is connected to drive the upper drive mechanism 190 under control of servo amplifier 310 while servomotor 430 is connected to drive the lower drive mechanism 195 under control of servo amplifier 320. The control system 260 is an all other respects similar to the one illustrated in FIG. 8.

The upper and lower mechanisms 190 and 195 connected to servomotors 350 and 430 move in accordance with a desired motion profile that is stored in the PAM 290 which directs the servo amplifier 310 and 320 to drive servomotors 350 and 430. The PAM software executes this motion profile through its control of the servo amplifiers 350 and 430.

In an alternative design to the control system 260 of FIG. 12, a single servomotor may be used to drive both the upper and lower drive mechanisms 190 and 195 with gearing disposed between the drive shaft 500 and the drive shaft 510 to effect the relative degree of cooperative movement.

Figure 13:
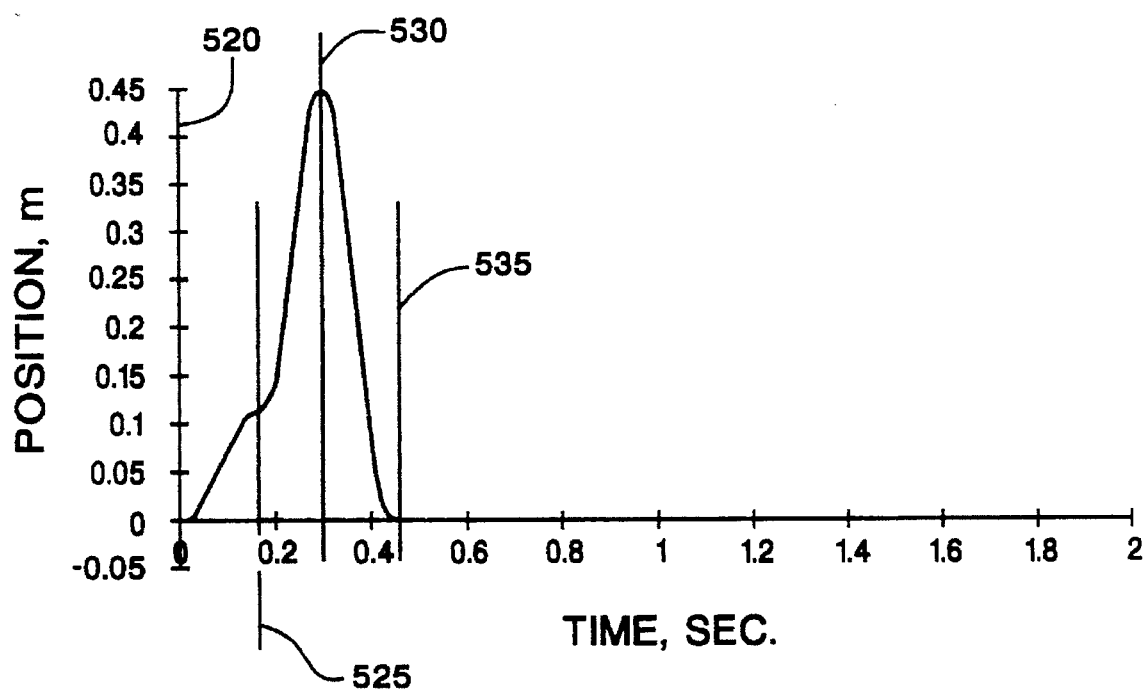
FIGS. 13–18 are graphs illustrating motion profiles that can be used in the control system of FIG. 12 to drive the lifter/folder mechanism of FIG. 7.
Figure 14:
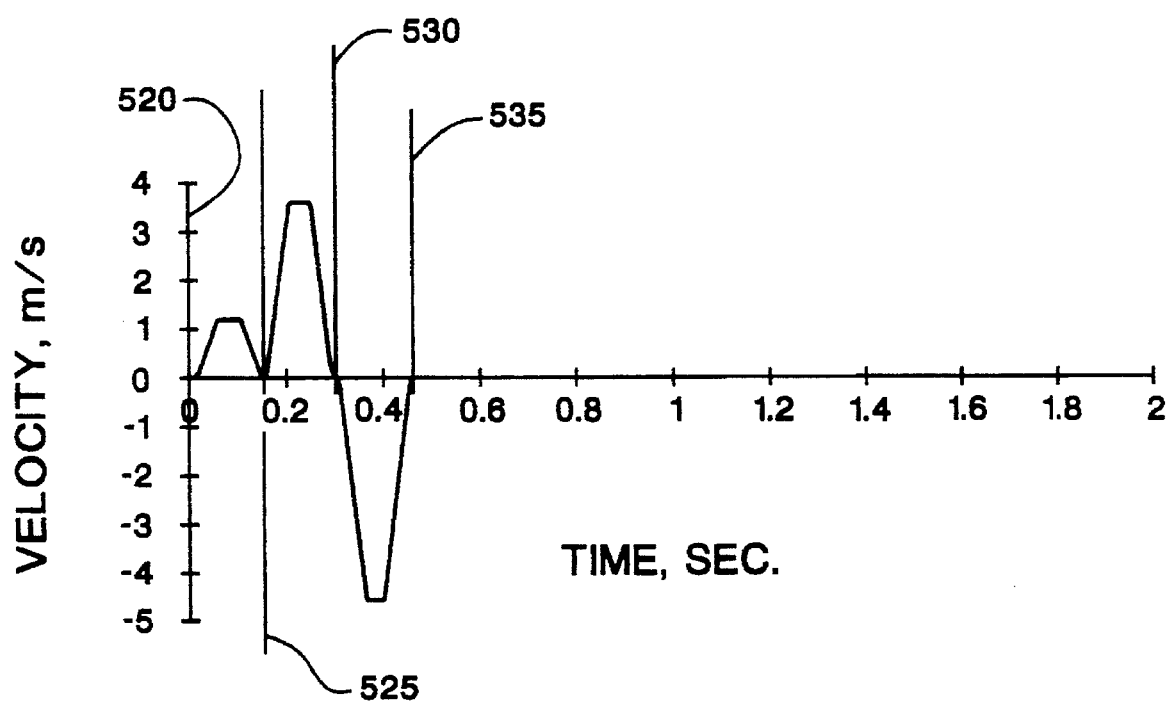
Figure 15:
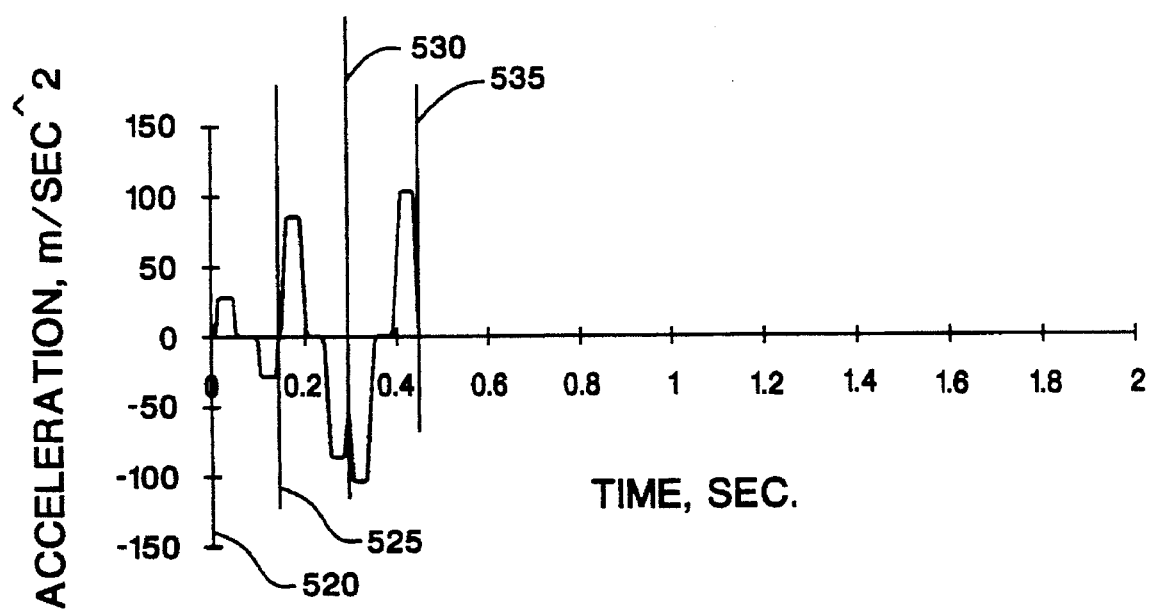

The pre-folder mechanism 180 includes both a top and bottom belt driven linear transport that may each move in accordance with its own motion profile stored in the PAM 290. The acceleration, velocity, and position profiles for the lower pre-folder mechanism 195 are set forth in FIGS. 13–15 as applied, for example, to the packaging machine of the aforementioned '546 application.

The lower pre-folder motion profile may include three moves. The servomotor 430 is first driven to lift the upwardly directed folder arms 225 to the bottoms of the cartons in the lower conveyor band in the time illustrated between lines 520 and 525 of each of FIGS. 13–15. The second move, shown between lines 525 and 530, drives the folder arms 225 up through the level of the lower conveyor band to the level of the upper conveyor band so that the bottom sealing areas of the cartons are in the same plane as the jaws of the horn and anvil of an ultrasonic bottom sealer. The third move, shown between lines 530 and 535 returns the upwardly directed folder arms 225 to their home position. The third move begins when the jaws of the bottom sealer make contact with the bottom sealing areas of the carton.

Each move of the lower pre-folder drive profile is a ⅓rd, ⅓rd, ⅓rd trapezoidal velocity profile. However, during the time of any acceleration (or deceleration) 20% of the time is spent ramping up to constant acceleration and 20% of the time is spent ramping down to zero acceleration thereby to limit jerking motions.

Figure 16:
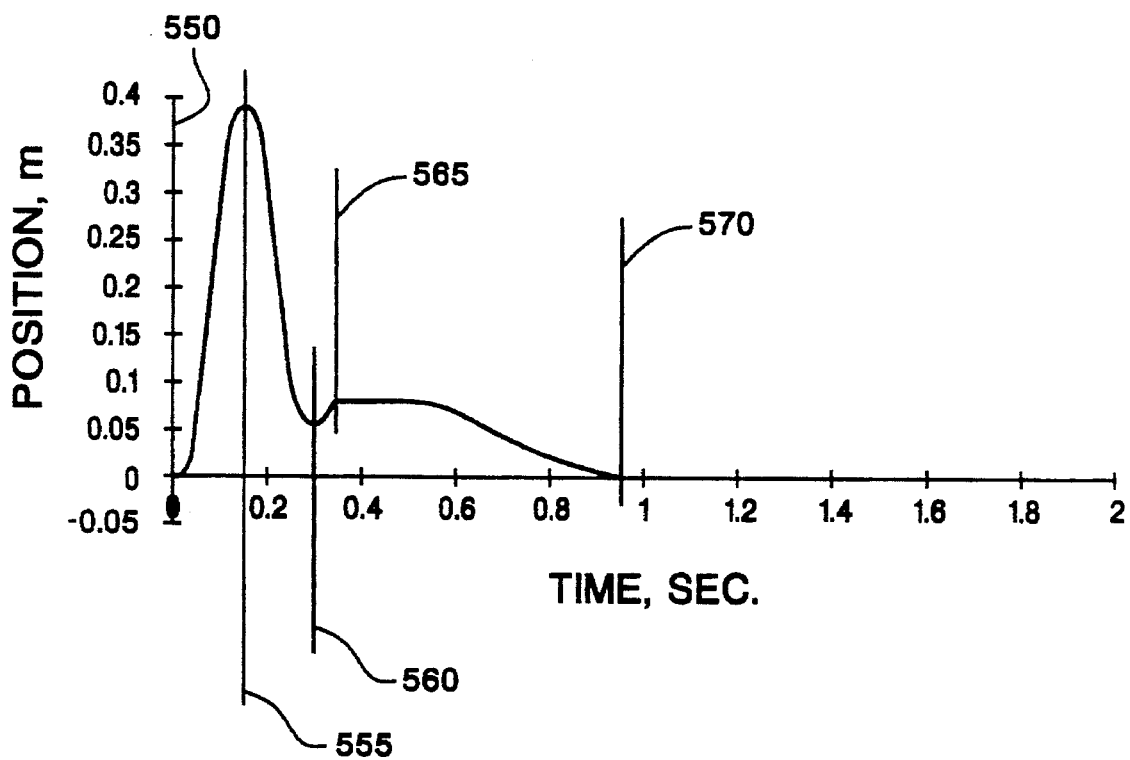
Figure 17:
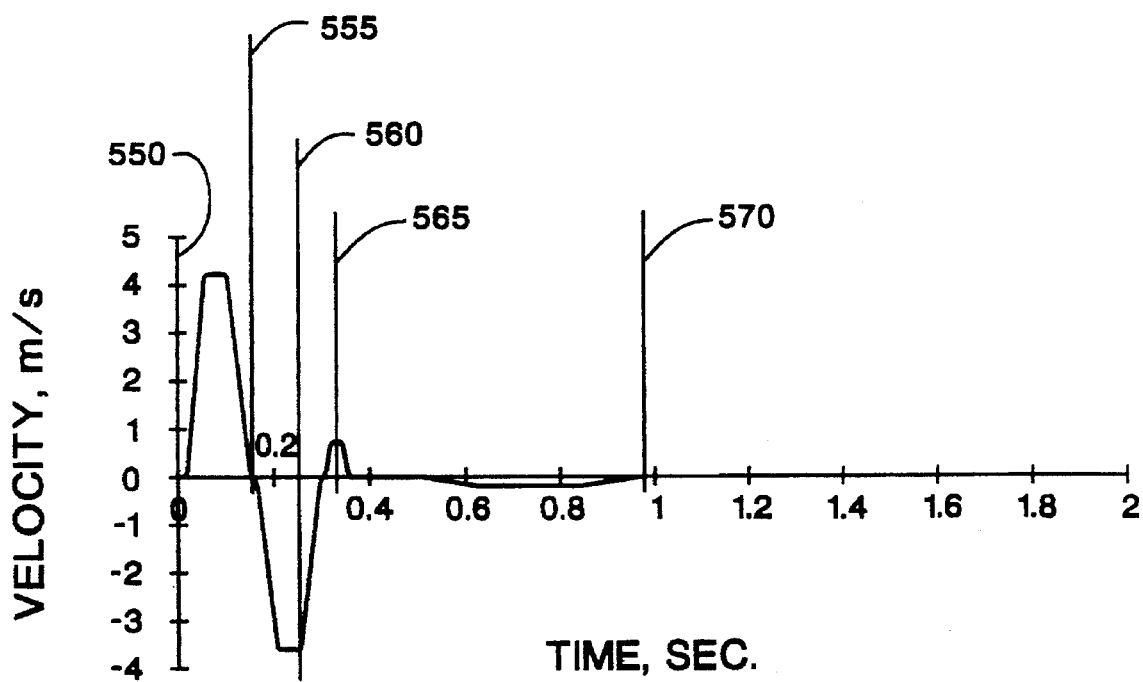
Figure 18:
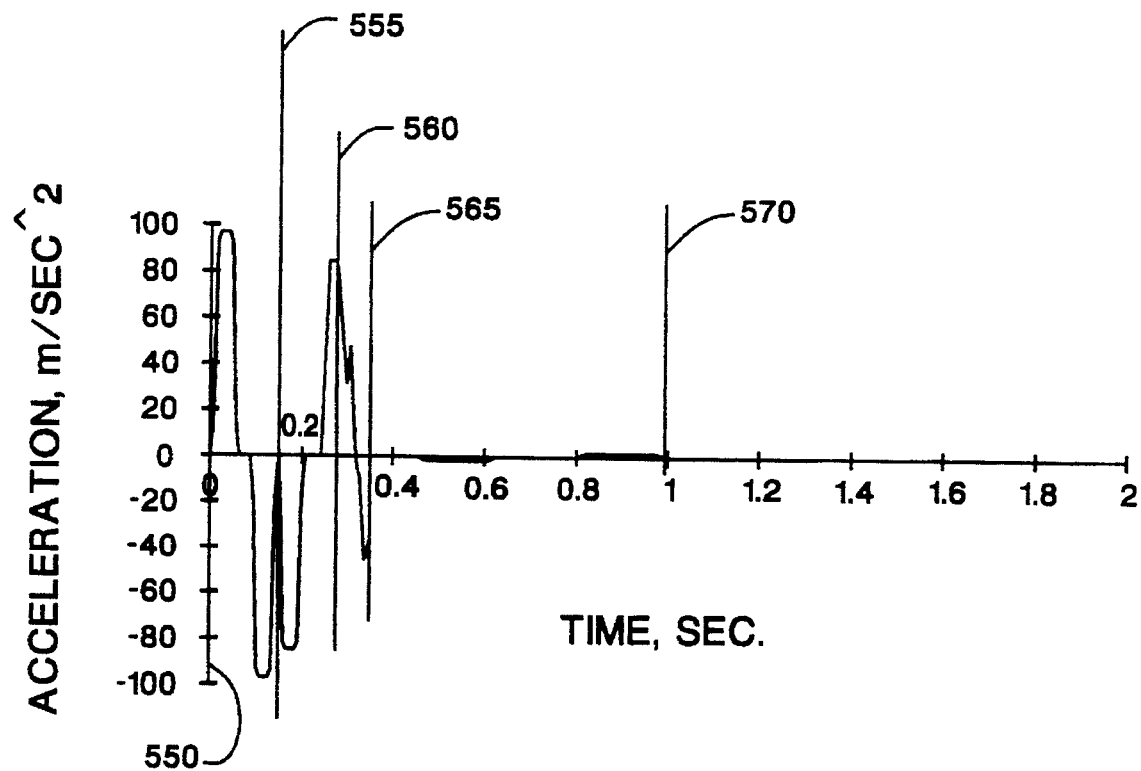

The motion profile for the upper belt driven linear transport mechanism of the upper pre-folder are illustrated in FIGS. 16–18. This profile may include four moves. The first servomotor move, shown between lines 550 and 555 of each of FIGS. 16–18 drives the downwardly directed folder arms 215 down through the level of the upper conveyor band into the level of the lower conveyor band at the level of the tops of the cartons in the lower conveyor band. Since the upwardly directed folder arms 225 arrive at the carton bottoms at approximately the same time, the bottom lift forks and the pre-folder forks secure the cartons.

The second move, shown between lines 555 and 560, draws the folder arms 215 back up to the level of the upper conveyor band. This second move is executed at the same time as the second move of the bottom pre-folder described above so that the cartons remain secure in the grips of both sets of folder arms 215 and 225 as they are transported between the conveyors.

The third move, shown between lines 560 and 656, drives the folder arms 215 down a length sufficient to keep the bottom sealing surfaces of the carton in the same plane as the bottom sealer jaws during jaw closure. Without this downward move of the folder arms, the bottom sealing surfaces of the carton may slide over the sealer jaws during their closure. The third move begins when the sealer jaws have made contact with the bottom sealing surfaces of the carton.

The fourth move, shown between lines 565 and 570 draws the folder arms 215 clear of the carton tops and returns them to their home position sometime before the upper conveyor band indexes the cartons from the pre-folder station. The retraction move begins after the sealer jaws have firmly gripped the carton bottoms.

Each move of the upper pre-folder motion profile is basically a ⅓rd, ⅓rd, ⅓rd trapezoidal velocity profile. During the time of any acceleration (or deceleration) 20% of the time is spent ramping up to constant acceleration and 20% of the time is spent ramping down to zero acceleration thereby to limit jerking of the mechanism. The ramping of accelerations was done in the uncertain belief that jerk-limited accelerations will be "easier" on the driven mechanisms.

The values set forth in the foregoing figures describing the exemplary motion profiles are in linear units (mm, mm/s, m, m/s, m/s^2) of travel instead of rotational measurement (radians or degrees) of servomotor rotation. In the illustrated embodiments of the linear drive, motor rotation is directly proportional to linear travel.

Figure 19:
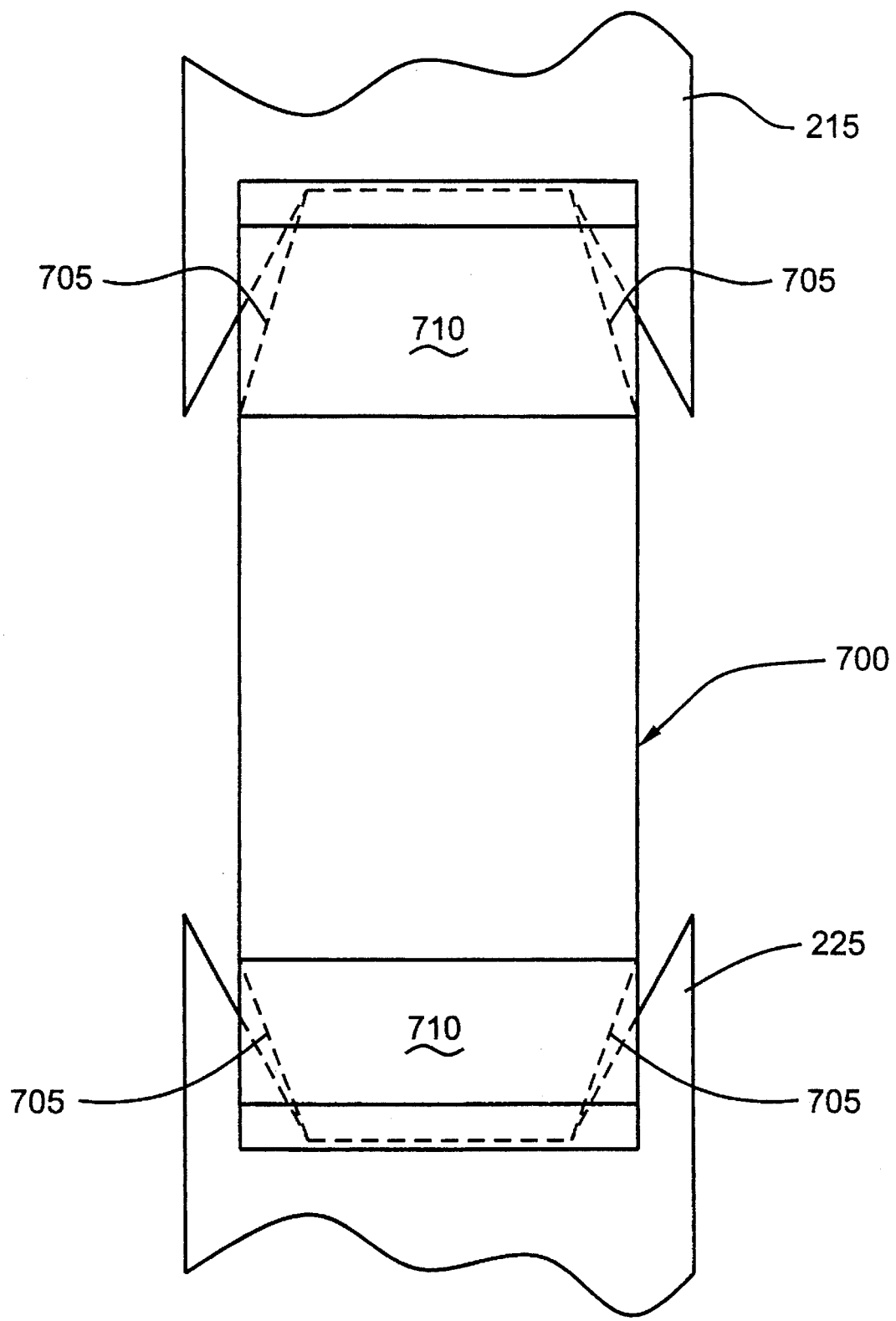
FIG. 19 illustrates engagement between the folder arms of the embodiment illustrated in FIG. 7 and a container having score lines defining upper and lower gabled sections.

FIG. 19 illustrates engagement between the folder arms 215 and 200 and a container 700. In the illustrated embodiment, the container 700 is an open rectangular blank having score lines defining a gabled top structure and a gabled bottom structure. As shown, the V-shaped sections of the folder arms 215 and 225 engage the side panels 705 that ultimately are turned beneath the roof panels 710 (only one top roof panel and one bottom roof panel shown) that define the gable top and bottom. Such a prefolding operation assists in preventing what is commonly known as "duckbilling" during subsequent top and bottom sealing operations.

Although the present invention has been described with reference to a specific embodiment, those of skill in the art will recognize that changes may be made thereto without departing from the scope and spirit of the invention as set forth in the appended claims.

We claim as our invention:

1. A linear driven pre-folder apparatus for a packaging machine, the apparatus comprising:

first and second spaced apart guide rods;

an engagement assembly disposed between the first and second spaced apart guide rods for sliding movement along the first and second guide rods between first and second positions, the engagement assembly comprising a first leg slidably engaging the first guide rod, a second leg slidably engaging the second guide rod, a bar extending between the first and second legs, a folder arm extending from the bar and having a generally V-shape recess shaped to engage and pre-fold a carton as the engagement assembly is moved from the first position to the second position;

a drive shaft;

a drive roller disposed for co-rotation with the drive shaft;

a first drive belt connected to the drive roller and disposed about the drive roller in a clockwise direction, the first drive belt extending from the drive roller and being connected to a first portion of the engagement assembly;

a second drive belt connected to the drive roller and disposed about the drive roller in a counter-clockwise direction, the second drive belt extending from the drive roller and being connected to a second portion of the engagement assembly opposite the first portion of the engagement assembly; and rotation of the drive shaft in a clockwise direction causing linear movement of the engagement assembly in a first direction along the guide rods, rotation of the drive shaft in a counter-clockwise direction causing linear movement of the engagement assembly in a second direction opposite the first direction; a further drive roller disposed for co-rotation with the drive shaft.

2. An apparatus as claimed in claim 1 and further comprising:

a further drive roller disposed for co-rotation with the drive shaft;

a third drive belt connected to the further drive roller and disposed about the further drive roller in a clockwise direction, the third drive belt extending from the further drive roller and being connected to a third portion of the engagement assembly; and a fourth drive belt connected to the further drive roller and disposed about the further drive roller in a counter-clockwise direction, the fourth drive belt extending from the further drive roller and being connected to a fourth portion of the engagement assembly, the first, second, third, and fourth portions of the engagement assembly forming corners of a parallelogram.

3. An apparatus as claimed in claim 2 and further comprising means for detecting breakage of the second and third drive belts.

4. An apparatus as claimed in claim 2 wherein the first and second drive rollers are disposed at opposite ends of the drive shaft and exterior to the first and second guide rods.

5. An apparatus as claimed in claim 1 and further comprising means for detecting breakage of the first and second drive belts.

6. An apparatus as claimed in claim 1 and further comprising means for controlling the rotation of the drive shaft.

7. An apparatus as claimed in claim 6 wherein the means for controlling comprises:

a servomotor connected to rotationally drive the drive shaft; and a servo amplifier connected to control the operation of the servomotor.

8. An apparatus as claimed in claim 7 and wherein the means for controlling further comprises a programmable axis manager connected to control the operation of the servomotor.

9. A linear driven apparatus for a packaging machine, the apparatus comprising:

first and second spaced apart guide rods;

a first leg slidably engaging the first guide rod;

a second leg slidably engaging the second guide rod;

an engagement bar extending between the first and second legs, the engagement bar adapted to engage a plurality of cartons;

a drive shaft;

a first drive roller disposed for co-rotation with the drive shaft;

a first drive belt connected to the first drive roller and disposed about the first drive roller in a clockwise direction, the first drive belt extending from the first drive roller and being connected to the first leg;

a second drive belt connected to the first drive roller and disposed about the first drive roller in a counter-clockwise direction, the second drive belt extending from the first drive roller and being connected to a first end of the engagement bar;

a second drive roller disposed for co-rotation with the drive shaft, the first and second drive rollers disposed at opposite ends of the drive shaft and exterior to the first and second guide rods;

a third drive belt connected to the second drive roller and disposed about the second drive roller in a clockwise direction, the third drive belt extending from the second drive roller and being connected to the second leg;

a fourth drive belt connected to the second drive roller and disposed about the second drive roller in a counter-clockwise direction, the fourth drive belt extending from the second drive roller and being connected to a second end of the engagement bar opposite the first end; and rotation of the drive shaft in a clockwise direction causing linear movement of the engagement bar and first and second legs in a first direction along the guide rods, rotation of the drive shaft in a counter-clockwise direction causing linear movement of the engagement bar and first and second legs in a second direction opposite the first direction.

10. An apparatus as claimed in claim 9 and further comprising means for detecting breakage of the first and second drive belts.

11. An apparatus as claimed in claim 9 and further comprising means for detecting breakage of the second and third drive belts.

12. An apparatus as claimed in claim 9 and further comprising means for controlling the rotation of the drive shaft.

13. An apparatus as claimed in claim 12 wherein the means for controlling comprises:

a servomotor connected to rotationally drive the drive shaft; and a servo amplifier connected to control the operation of the servomotor.

14. An apparatus as claimed in claim 9 wherein the means for controlling further comprises a programmable axis manager connected to control the operation of the servomotor.

15. A linear driven pre-folder apparatus for a packaging machine, the apparatus comprising:

first and second spaced apart guide rods;

a first leg slidably engaging the first guide rod;

a second leg slidably engaging the second guide rod;

an engagement bar extending between the first and second legs and movable along the first and second spaced apart guide rods between a first and a second position;

a plurality of folder arms in fixed alignment with the engagement bar, each of the plurality of folder arms including a generally V-shaped recess shaped to engage and pre-fold a respective carton as the engagement bar moves between the first and second positions;

a drive shaft;

a first drive roller disposed for co-rotation with the drive shaft;

a first drive belt connected to the first drive roller and disposed about the first drive roller in a clockwise direction, the first drive belt extending from the first drive roller and being connected to the engagement bar;

a second drive belt connected to the first drive roller and disposed about the first drive roller in a counterclockwise direction, the second drive belt extending from the first drive roller and being connected to the first leg;

a second drive roller disposed for co-rotation with the drive shaft;

a third drive belt connected to the second drive roller and disposed about the second drive roller in a clockwise direction, the third drive belt extending from the second drive roller and being connected to the engagement bar;

a fourth drive belt connected to the second drive roller and disposed about the second drive roller in a counter-clockwise direction, the fourth drive belt extending from the second drive roller and being connected to the second leg; and rotation of the drive shaft in a clockwise direction causing linear movement of the engagement bar and first and second legs in a first direction along the guide rods, rotation of the drive shaft in a counter-clockwise direction causing linear movement of the engagement bar and first and second legs in a second direction opposite the first direction.

16. An apparatus as claimed in claim 15 and further comprising means for detecting breakage of the first and second drive belts.

17. An apparatus as claimed in claim 16 and further comprising means for detecting breakage of the second and third drive belts.

18. An apparatus as claimed in claim 15 and further comprising means for controlling the rotation of the drive shaft.

19. An apparatus as claimed in claim 18 wherein the means for controlling comprises:

a servomotor connected to rotationally drive the drive shaft; and a servo amplifier connected to control the operation of the servomotor.

20. An apparatus as claimed in claim 19 wherein the means for controlling further comprises a programmable axis manager connected to control the operation of the servomotor.

21. An apparatus as claimed in claim 15 wherein the first and second drive rollers are disposed at opposite ends of the drive shaft and exterior to the first and second guide rods.

22. A pre-folder mechanism for pre-folding a carton and moving the carton from a first conveyor assembly to a second conveyor assembly, the pre-folder mechanism comprising:

first and second spaced apart guide rods;

a first pre-folder assembly disposed between the first and second spaced apart guide rods for sliding movement along the first and second guide rods, the first pre-folder assembly including at least one folder arm that assists in pre-folding a first end of the carton when the carton is engaged by the at least one folder arm of the first pre-folder assembly;

a first drive shaft;

a first drive roller disposed for co-rotation with the drive shaft;

a first drive belt connected to the first drive roller and disposed about the first drive roller in a clockwise direction, the first drive belt extending from the first drive roller and being connected to a first portion of the first pre-folder assembly;

a second drive belt connected to the first drive roller and disposed about the first drive roller in a counter-clockwise direction, the second drive belt extending from the first drive roller and being connected to a second portion of the first pre-folder assembly opposite the first portion of the first pre-folder assembly;

a second pre-folder assembly disposed between the first and second spaced apart guide rods for sliding movement along the first and second guide rods, the second pre-folder assembly including at least one folder arm that assists in pre-folding a second end of the carton when the carton is engaged by the at least one folder arm of the second pre-folder assembly;

a second drive shaft;

a second drive roller disposed for co-rotation with the drive shaft;

a third drive belt connected to the second drive roller and disposed about the second drive roller in a clockwise direction, the third drive belt extending from the second drive roller and being connected to a first portion of the second pre-folder assembly;

a fourth drive belt connected to the second drive roller and disposed about the second drive roller in a counter-clockwise direction, the fourth drive belt extending from the second drive roller and being connected to a second portion of the second pre-folder assembly opposite the first portion of the second pre-folder assembly; and rotation of the first drive shaft causing linear movement of the first pre-folder assembly along the first and second guide rods, rotation of the second drive shaft causing linear movement of the second pre-folder assembly along the first and second guide rods, the first and second drive shafts being rotatable to cause said first and second pre-folder assemblies to move linearly toward one another and away from one another along the first and second guide rods.

23. An apparatus as claimed in claim 22 and further comprising:

a third drive roller disposed for co-rotation with the first drive shaft;

a fifth drive belt connected to the third drive roller and disposed about the third drive roller in a clockwise direction, the fifth drive belt extending from the third drive roller and being connected to a third portion of the first pre-folder assembly; and a sixth drive belt connected to the third drive roller and disposed about the third drive roller in a counter-clockwise direction, the sixth drive belt extending from the third drive roller and being connected to a fourth portion of the first pre-folder assembly, the first, second, third, and fourth portions of the first pre-folder assembly forming corners of a parallelogram.

24. An apparatus as claimed in claim 23 further comprising:

a fourth drive roller disposed for co-rotation with the second drive shaft;

a seventh drive belt connected to the fourth drive roller and disposed about the fourth drive roller in a clockwise direction, the seventh drive belt extending from the fourth drive roller and being connected to a third portion of the second pre-folder assembly; and an eighth drive belt connected to the fourth drive roller and disposed about the fourth drive roller in a counter-clockwise direction, the eighth drive belt extending from the fourth drive roller and being connected to a fourth portion of the second pre-folder assembly, the first, second, third, and fourth portions of the second pre-folder assembly forming corners of a parallelogram.

25. An apparatus as claimed in claim 22 further comprising means for controlling the rotation of the first and second drive shafts.

26. An apparatus as claimed in claim 25 wherein the means for controlling comprises:
   a first servomotor connected to rotationally drive the first drive shaft;
   a first servo amplifier connected to control the operation of the first servomotor;
   a second servomotor connected to rotationally drive the second drive shaft; and
   a second servo amplifier connected to control the operation of the second servomotor.

27. An apparatus as claimed in claim 26 wherein the means for controlling further comprises
   a programmable axis manager connected to control the operation of the first and second servo amplifiers.

28. A linear drive apparatus for a packaging machine, the apparatus comprising:
   first and second spaced apart guide rods;
   a first leg slidably engaging the first guide rod;
   a second leg slidably engaging the second guide rod;
   an engagement bar extending between the first and second legs, the engagement bar adapted to engage a plurality of cartons;
   a drive shaft;
   a first drive roller disposed for co-rotation with the drive shaft;
   a first drive belt connected to the first drive roller and disposed about the first drive roller in a clockwise direction, the first drive belt extending from the first drive roller and being connected to the engagement bar;
   a second drive belt connected to the first drive roller and disposed about the first drive roller in a counter-clockwise direction, the second drive belt extending from the first drive roller and being connected to the first leg;
   a second drive roller disposed for co-rotation with the drive shaft, the first and second drive rollers being disposed at opposite ends of the drive shaft and exterior to the first and second guide rods;
   a third drive belt connected to the second drive roller and disposed about the second drive roller in a clockwise direction, the third drive belt extending from the second drive roller and being connected to the engagement bar;
   a fourth drive belt connected to the second drive roller and disposed about the second drive roller in a counter-clockwise direction, the fourth drive belt extending from the second drive roller and being connected to the second leg; and
   rotation of the drive shaft in a clockwise direction causing linear movement of the engagement bar and first and second legs in a first direction along the guide rods, rotation of the drive shaft in a counter-clockwise direction causing linear movement of the engagement bar and first and second legs in a second direction opposite the first direction.

29. An apparatus as claimed in claim 28 and further comprising means for detecting breakage of the first and second drive belts.

30. An apparatus as claimed in claim 29 and further comprising means for detecting breakage of the second and third drive belts.

31. An apparatus as claimed in claim 28 and further comprising means for controlling the rotation of the drive shaft.

32. An apparatus as claimed in claim 31 wherein the means for controlling comprises:
   a servomotor connected to rotationally drive the drive shaft; and
   a servo amplifier connected to control the operation of the servomotor.

33. An apparatus as claimed in claim 32 wherein the means for controlling further comprises a programmable axis manager connected to control the operation of the servomotor.

34. An apparatus for a packaging machine, the apparatus comprising:
   first and second spaced apart guide rods;
   an engagement assembly disposed between the first and second spaced apart guide rods for sliding movement along the first and second guide rods between first and second positions, the engagement assembly comprising a folder arm extending therefrom having a generally V-shaped recess shaped to engage and pre-fold a carton as the engagement assembly is moved from the first position to the second position;
   a drive shaft;
   a drive roller disposed for co-rotation with the drive shaft;
   a first drive belt connected to the drive roller and disposed about the drive roller in a clockwise direction, the first drive belt extending from the drive roller and being connected to a first portion of the engagement assembly;
   a second drive belt connected to the drive roller and disposed about the drive roller in a counter-clockwise direction, the second drive belt extending from the drive roller and being connected to a second portion of the engagement assembly opposite the first portion of the engagement assembly; and
   rotation of the drive shaft in a clockwise direction causing linear movement of the engagement assembly in a first direction along the guide rods, rotation of the drive shaft in a counter-clockwise direction causing linear movement of the engagement assembly in a second direction opposite the first direction.

35. An apparatus as claimed in claim 34 wherein the engagement assembly comprises:
   a first leg slidably engaging the first guide rod, the first leg having a lower portion, the lower portion of the first leg being connected to the second drive belt;
   a second leg slidably engaging the second guide rod; and
   a bar extending between the first and second legs.

36. An apparatus as claimed in claim 34 wherein the engagement assembly comprises a folder arm having a generally V-shaped recess, the folder arm shaped to engage the carton in the V-shaped recess to pre-fold the carton as the engagement assembly is moved from the first position to the second position.

37. An apparatus as claimed in claim 34 and further comprising:
   a further drive roller disposed for co-rotation with the drive shaft;
   a third drive belt connected to the further drive roller and disposed about the further drive roller in a clockwise direction, the third drive belt extending from the further drive roller and being connected to a third portion of the engagement assembly; and a fourth drive belt connected to the further drive roller and disposed about the further drive roller in a counter-clockwise direction, the fourth drive belt extending from the further drive roller and being connected to a fourth portion of the engagement assembly, the first, second, third, and fourth portions of the engagement assembly forming corners of a parallelogram.

38. An apparatus as claimed in claim 37 and further comprising means for detecting breakage of the second and third drive belts.

39. An apparatus as claimed in claim 37 wherein the drive roller and further drive roller are disposed at opposite ends of the drive shaft and exterior to the first and second guide rods.

40. An apparatus as claimed in claim 34 and further comprising means for detecting breakage of the first and second drive belts.

41. An apparatus as claimed in claim 34 and further comprising means for controlling the rotation of the drive shaft.

42. An apparatus as claimed in claim 41 wherein the means for controlling comprises:

a servomotor connected to rotationally drive the drive shaft; and a servo amplifier connected to control the operation of the servomotor.

43. An apparatus as claimed in claim 42 wherein the means for controlling further comprises a programmable axis manager connected to control the operation of the servomotor.

44. An apparatus for lifting a carton in a packaging machine, the apparatus comprising:

first and second spaced apart guide rods;

an engagement assembly disposed between the first and second spaced apart guide rods for sliding movement along the first and second guide rods between first and second positions, the engagement assembly comprising a carton gripper extending therefrom to grip and move a carton as the engagement assembly is moved vertically from the first position to the second position, the carton gripper being shaped to grip and conform to a gabled bottom of the carton;

a drive shaft;

a drive roller disposed for co-rotation with the drive shaft;

first drive belt connected to the drive roller and disposed about the drive roller in a clockwise direction, the first drive belt extending from the drive roller and being connected to a first portion of the engagement assembly;

a second drive belt connected to the drive roller and disposed about the drive roller in a counter-clockwise direction, the second drive belt extending from the drive roller and being connected to a second portion of the engagement assembly opposite the first portion of the engagement assembly; and rotation of the drive shaft in a clockwise direction causing linear movement of the engagement assembly in a first direction along the guide rods, rotation of the drive shaft in a counter-clockwise direction causing linear movement of the engagement assembly in a second direction opposite the first direction.

45. An apparatus as claimed in claim 44 wherein the engagement assembly comprises:

a first leg slidably engaging the first guide rod, the first leg having a lower portion, the lower portion of the first leg being connected to the second drive belt;

a second leg slidably engaging the second guide rod; and a bar extending between the first and second legs.

46. An apparatus as claimed in claim 44 and further comprising:

a further drive roller disposed for co-rotation with the drive shaft;

a third drive belt connected to the further drive roller and disposed about the further drive roller in a clockwise direction, the third drive belt extending from the further drive roller and being connected to a third portion of the engagement assembly; and a fourth drive belt connected to the further drive roller and disposed about the further drive roller in a counter-clockwise direction, the fourth drive belt extending from the further drive roller and being connected to a fourth portion of the engagement assembly, the first, second, third, and fourth portions of the engagement assembly forming corners of a parallelogram.

47. An apparatus as claimed in claim 46 and further comprising means for detecting breakage of the second and third drive belts.

48. An apparatus as claimed in claim 46 wherein the drive roller and further drive roller are disposed at opposite ends of the drive shaft and exterior to the first and second guide rods.

49. An apparatus as claimed in claim 44 and further comprising means for detecting breakage of the first and second drive belts.

50. An apparatus as claimed in claim 44 and further comprising means for controlling the rotation of the drive shaft.

51. An apparatus as claimed in claim 50 wherein the means for controlling comprises:

a servomotor connected to rotationally drive the drive shaft; and a servo amplifier connected to control the operation of the servomotor.

52. An apparatus as claimed in claim 51 and wherein the means for controlling further comprises a programmable axis manager connected to control the operation of the servomotor.

53. A linear drive apparatus for a packaging machine, the apparatus comprising:

first and second spaced apart guide rods;

an engagement assembly disposed between the first and second spaced apart guide reds for sliding movement along the first and second guide rods, the engagement assembly including a carton engagement structure shaped to engage a gabled bottom of a carton as the engagement assembly is moved between the first and second positions;

a drive shaft;

a first drive roller disposed for co-rotation with the drive shaft;

a first drive belt connected to the first drive roller and disposed about the first drive roller in a clockwise direction, the first drive belt extending from the first drive roller and being connected to a first portion of the engagement assembly;

a second drive belt connected to the first drive roller and disposed about the first drive roller in a counter-clockwise direction, the second drive belt extending from the first drive roller and being connected to a second portion of the engagement assembly opposite the first portion of the engagement assembly;

a second drive roller disposed for co-rotation with the drive shaft, the first and second drive rollers disposed at opposite ends of the drive shaft and exterior to the first and second guide rods;

a third drive belt connected to the second drive roller and disposed about the second drive roller in a clockwise direction, the third drive belt extending from the second drive roller and being connected to a third portion of the engagement assembly;

a fourth drive belt connected to the second drive roller and disposed about the second drive roller in a counter-clockwise direction, the fourth drive belt extending from the second drive roller and being connected to a fourth portion of the engagement assembly, the first, second, third, and fourth portions of the engagement assembly forming corners of a parallelogram;

rotation of the drive shaft in a clockwise direction causing linear movement of the engagement assembly in a first direction along the guide rods, rotation of the drive shaft in a counter-clockwise direction causing linear movement of the engagement assembly in a second direction opposite the first direction.

54. An apparatus as claimed in claim 53 wherein the carton engagement structure is a carton gripper.

55. An apparatus as claimed in claim 53 wherein the carton engagement structure is a carton pre-folder.

* * * * *